United States Patent [19]

Lary et al.

[11] Patent Number: 5,713,913
[45] Date of Patent: Feb. 3, 1998

[54] DEVICE AND METHOD FOR TRANSECTING A CORONARY ARTERY

[75] Inventors: Banning G. Lary; Paul W. Mayer, both of Miami, Fla.

[73] Assignee: InterVentional Technologies Inc., San Diego, Calif.

[21] Appl. No.: 747,187

[22] Filed: Nov. 12, 1996

[51] Int. Cl.$^6$ ..................................... A61M 29/00
[52] U.S. Cl. ................. 606/159; 606/194; 604/96
[58] Field of Search ................ 604/96–103; 606/191, 606/194, 195, 159, 170, 180

[56] References Cited

U.S. PATENT DOCUMENTS

| | | |
|---|---|---|
| 2,816,552 | 12/1957 | Hoffman . |
| 3,635,223 | 1/1972 | Klieman . |
| 4,140,126 | 2/1979 | Choudhury . |
| 4,273,128 | 6/1981 | Lary . |
| 4,574,781 | 3/1986 | Chin . |
| 4,685,458 | 8/1987 | Leckrone . |
| 4,784,636 | 11/1988 | Rydell . |
| 4,886,061 | 12/1989 | Fischell et al. . |
| 4,895,166 | 1/1990 | Farr et al. . |
| 4,936,845 | 6/1990 | Stevens . |
| 5,009,659 | 4/1991 | Hamlin et al. . |
| 5,084,061 | 1/1992 | Gau et al. ................. 604/103 |
| 5,158,564 | 10/1992 | Schnepp-Pesch et al. . |
| 5,196,024 | 3/1993 | Barath ..................... 606/159 |
| 5,209,730 | 5/1993 | Sullivan .................. 606/194 |
| 5,209,749 | 5/1993 | Buelna .................... 606/159 |
| 5,209,799 | 5/1993 | Vigil . |
| 5,320,634 | 6/1994 | Vigil et al. . |
| 5,336,234 | 8/1994 | Vigil et al. ............... 606/159 |
| 5,372,601 | 12/1994 | Lary . |

FOREIGN PATENT DOCUMENTS

WO 90/07909  7/1990  WIPO .

OTHER PUBLICATIONS

Baning G. Lary, M.D., *Method for Increasing the Diameter of Long Segments of the Coronary Artery*, pp. 33–35, Jan., 1966, vol. 32, No. 1, The American Surgeon.

Banning G. Lary, M.D. and Roger W. Sherman, M.D., *A method for creating a coronary–myocardial artery*, pp. 1061–1064, Jun. 1966, vol. 59, No. 6, Surgery.

Banning G. Lary, M.D., *A Method to Create and Correct Stenosis of a Coronary Artery*, pp. 828–830, Nov. 1966, vol. 93, Archives of Surgery.

Banning G. Lary, M.D., *Coronary Artery Incision and Dilation*, pp. 1478–1480, Dec. 1980, vol. 115, Archives of Surgery.

*Primary Examiner*—William Lewis
*Attorney, Agent, or Firm*—Nydegger & Associates

[57] ABSTRACT

The present invention is a device for creating a transection in a coronary artery. Structurally, the present invention includes an inflatable balloon mounted at the distal end of a catheter. A single blade is mounted to project radially from the surface of the balloon and is aligned with the balloon's longitudinal axis. Additionally, a series of radio-opaque markers are distributed on the balloon's surface. Operationally, the balloon is advanced, using the catheter, until it is positioned at the approximate site of the desired transection. An X-ray imaging system is then used to visualize the radio-opaque markers, allowing the balloon and blade to be oriented radially and longitudinally at the location required for the transection. The balloon is then inflated, forcing the blade to incise the artery wall and creating the desired transection. The transection creates a new artery composed partially of the old artery and partially of the surrounding fibrous tissue.

17 Claims, 2 Drawing Sheets

DEVICE AND METHOD FOR TRANSECTING A CORONARY ARTERY

FIELD OF THE INVENTION

The present invention pertains generally to surgical instruments. More particularly, the present invention pertains to invasive surgical devices which are useful for the incision of a coronary artery. The present invention is particularly, though not exclusively, useful to transect the side of a coronary artery which is closest to the heart to effectively form a new artery.

BACKGROUND OF THE INVENTION

Over the years, the blockage of human arteries has become a leading medical concern. This is so because a variety of serious medical complications may result from arterial blockages that reduce blood flow through an affected artery. More specifically, an arterial blockage may result in damage to the tissue that relies on the artery for its blood supply. For example, if a blockage occurs in an artery leading to the brain, a stroke may result. Similarly, if a blockage occurs in an artery which supplies blood to the heart, a heart attack may result.

Typically, arterial blockages are caused by the build-up of atherosclerotic plaque on the inside wall of the artery. These blockages, which are commonly called stenoses, may result in a partial, or even complete, blockage of the artery. As a result of the dangers associated with these arterial blockages, a variety of procedures have been developed to treat them. An angioplasty procedure is, perhaps, the most commonly used procedure for such treatment. An angioplasty procedure involves the use of an inflatable angioplasty balloon to dilate the blocked artery. A typical inflatable angioplasty device, for example, is disclosed in U.S. Pat. No. 4,896,669 which issued to Bhate et al. for an invention entitled "DILATION CATHETER." The Bhate et al. angioplasty device includes an inflatable angioplasty balloon which is insertable into a peripheral artery of a patient for positioning across a stenosis. Once positioned, the angioplasty balloon is then inflated to dilate the stenosis within the artery thereby improving the blood flow through the artery.

While angioplasty balloons have been widely accepted for the treatment of stenoses, recent studies have indicated that the efficacy of the dilation of a stenosis is enhanced by first, or simultaneously, incising the material that is creating the stenosis. Not surprisingly then, angioplasty balloons have been equipped with cutting edges, or atherotomes. These cutting edges are intended to incise the stenosis during the angioplasty procedure to facilitate dilation of the stenosis. An example of an angioplasty balloon equipped with cutting edges is disclosed in U.S. Pat. No. 5,196,024 which issued to Barath for an invention entitled "BALLOON CATHETER WITH CUTTING EDGE," and which is assigned to the assignee of the present invention. The Barath device includes an inflatable angioplasty balloon with a number of atherotomes mounted longitudinally on its surface. During the inflation of the Barath balloon, the atherotomes induce a series of longitudinal cuts into the stenotic material as the balloon expands to dilate the stenosis. As a result of such longitudinal cuts, the stenosis is more easily dilated, and the likelihood of damaging the artery during dilation is significantly reduced.

In general, the use of angioplasty has been found to be an effective means for reducing arterial blockage associated with the buildup of atherosclerotic plaque. In some cases, however, it has been found that the atherosclerotic plaque which forms a particular stenotic segment may be too rigid to be effectively dilated. In such cases, traditional angioplasty techniques have been found to be largely ineffective and, in some cases, even harmful. As a result, a number of differing techniques have been developed for the treatment of hardened, or rigid stenotic segments. One such technique, which is specifically targeted at the coronary arteries, is transection. Transection, as applied to the coronary arteries, involves the creation of an elongated incision within the artery where the targeted stenosis is located. More specifically, a longitudinally oriented incision is created which spans the targeted stenosis and is positioned along the wall of the artery which is closest to the cardiac muscle. Creation of the incision causes the formation of a new arterial segment, with the new segment being composed partially of the previously occluded artery, and partially of the fibrous material of the heart. The new arterial segment evolves from the blood clot that forms when the arterial wall is transectioned. Effectively then, transection overcomes the occluding effect of atherosclerotic plaque by allowing the occluded artery to expand into the fibrous material of the heart. A description of this procedure is provided in "Coronary Artery Incision and Dilation" Archives of Surgery, December 1980, Volume 115, Pages 1478–1480, by Banning Gray Lary, M.D.

For the transection procedure to succeed, it is critical that the incision be made on the portion of the coronary artery which directly faces the heart muscle. This is so because the transection procedure involves cutting through the arterial wall, a procedure which would ordinarily result in an uncontrolled blood loss and, perhaps, the death of the patient. However, if the transection is made on the portion of the artery against the heart, the epicardial tissues which cover the heart and the coronary arteries prevent the loss of blood, allowing the new artery to form.

Unfortunately, in the context of a transection procedure, currently available angioplasty balloons have a particular disadvantage. More specifically, practice has shown that it is generally difficult to direct the atherotomes of a traditional angioplasty balloon with the accuracy required for a successful transection. Instead, when a traditional angioplasty balloon is employed, there is an ever present danger that the transection will be created in a part of the arterial wall that is not adjacent to the heart. Specifically, there is a present inability to precisely control the position an angioplasty balloon and cutting edge in both a longitudinal and a rotational direction.

Another disadvantage associated with the use of traditional angioplasty balloons for the creation of coronary transections involves the depth of the created incision. More specifically, practice has demonstrated that effective transection requires that the created incision be deep enough to allow the new artery to form.

Accordingly, it is an object of the present invention to provide a device for longitudinally transecting a coronary artery. It is a further object of the present invention to provide a device capable of accurately locating a transection, in both a longitudinal and a rotational direction, within an artery. It is another object of the present invention to provide a device capable of producing a transection at a depth favorable to arterial formation. It is yet another object of the present invention to provide a device for transecting a coronary artery which is relatively easy to use, easy to manufacture, and comparatively cost effective.

SUMMARY OF THE PREFERRED EMBODIMENTS

The present invention is a device for transecting a coronary artery. Structurally, the present invention includes an inflatable balloon mounted at the distal end of a flexible catheter. The balloon is preferably of the traditional angioplasty type and is connected in fluid communication with an inflation lumen which passes through the catheter. A single blade, or atherotome, is attached to the surface of the inflatable balloon and aligned with the longitudinal axis of the balloon. The blade has an elongated cutting edge which extends radially away from the surface of the balloon. Thus, when the angioplasty balloon is positioned within a coronary artery and inflated, the cutting blade moves radially outward to transect the arterial wall.

A series of radio-opaque markers are attached to the surface of the inflatable balloon. The markers are distributed on the balloon using a configuration which allows the longitudinal and rotational position of the cutting blade to be identified using a standard X-ray imaging system. In this way, by viewing the X-ray imaging system while simultaneously positioning the device within a patient's coronary artery, the precise positioning of the cutting blade required for the successful transection may be attained.

Preferably, the catheter is formed with a guidewire lumen which extends through the length of the catheter and through the inflatable balloon. The guidewire lumen is dimensioned to receive a guidewire, which may be chosen from a wide range of medical guidewire types.

Operation of the present invention begins with insertion the guidewire into the artery of a patient and subsequent advancement of the guidewire until the distal end of the guidewire is positioned near the site of the stenosis targeted by the transection procedure. The extracorporeal end of the guidewire is then threaded through the guidewire lumen of the device of the present invention. The balloon and catheter of the device are then advanced over the guidewire and into the artery of the patient. Specifically, the balloon is advanced over the guidewire until it is near the stenotic segment that is targeted by the transection procedure. At this point, the X-ray imaging system is activated and used to visualize the device within the patient's body. Using the X-ray image, and in particular, by noting the position and orientation of the radio-opaque markers, the device is positioned longitudinally and rotationally to orient the blade over the desired location of the transection. The balloon is then inflated and the expanding balloon forces the blade to incise the wall of the artery creating the desired transection.

After the initial transection has been completed, the angioplasty balloon is deflated and may be re-positioned within the artery to perform yet another transection. Using this step-and-repeat manner, a transection having a substantial length may be created. Once completed, the transection functions as a new artery, with part of the artery being composed of the formerly occluded artery and part of the artery being composed of the surrounding fibrous tissue, which occurs from the maturation of the initial blood clot.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
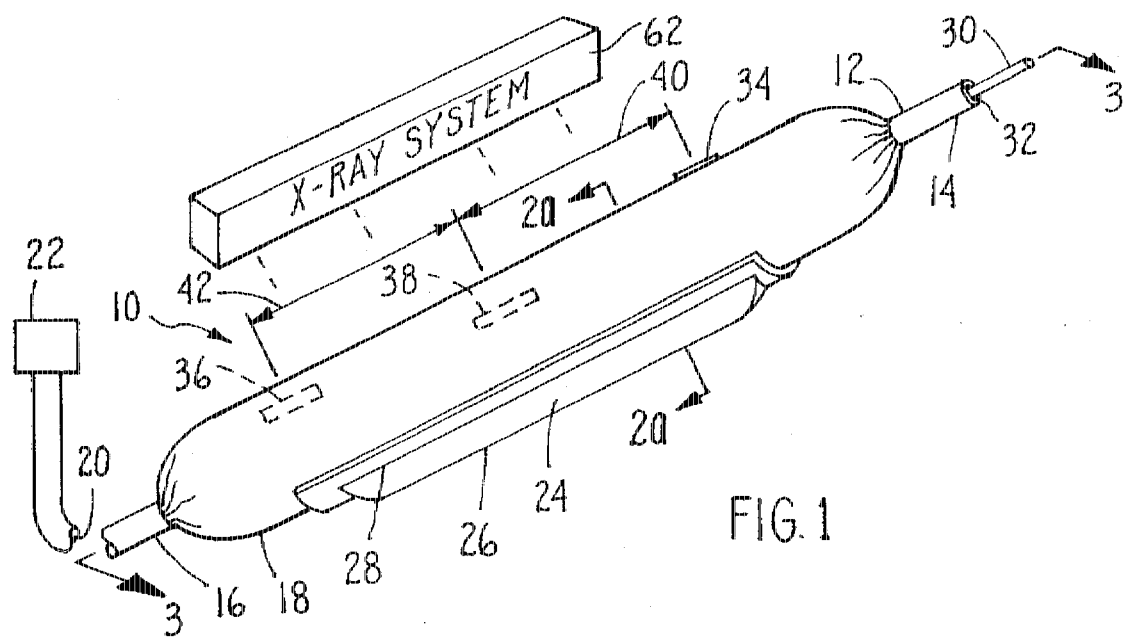
FIG. 1 is a perspective view of the present invention.

The present invention is a device for transecting a coronary artery. The structural components of the present invention are best appreciated by initial reference to FIG. 1 where the device of the present invention is shown and generally designated 10. In more detail, it may be seen that device 10 includes a catheter 12 having a distal end 14 and a proximal end 16. An inflatable balloon 18 is attached to the distal end 14 of the catheter 12. The balloon 18 is preferable of the traditional angioplasty type and is connected in fluid communication with an inflation lumen 20 which passes through the catheter 12. A fluid pump 22 is attached to the proximal end 16 of the catheter 12. The fluid pump 22, like the balloon 18, is attached in fluid communication with the inflation lumen 20. Functionally, the connection between the balloon 18, inflation lumen 20 and fluid pump 22, allows the fluid pump 22 to selectively pass fluid through the catheter 12 to selectively inflate the balloon 18. Specifically, the fluid pump 22 may be used to cause the balloon 18 to move between a first configuration, where the balloon 18 has a reduced radius and a second configuration where the balloon 18 has an increased radius.

Continuing with FIG. 1, it may be seen that the present invention includes a blade, or atherotome 24. The blade 24 is formed with a sharpened cutting edge 26 and a base 28. Blade 24 is longitudinal aligned with balloon 18 and the base 28 of the blade 24 is attached to the surface of the balloon 18. Importantly, the blade 24 is dimensioned so that cutting edge 26 exceeds the surface of the balloon 18 by a distance chosen so that the blade 24 may incise the wall of a coronary artery. Generally, the blade 24 may be fabricated from a range of materials including plastics and composites. For the purposes of the present invention, however, it has been found especially practical to fabricate the blade 24 from stainless steel.

Preferably, the present invention includes a guidewire, such as the guidewire 30 shown in FIG. 1. The guidewire 30 is generally of the type generally used for angioplasty type procedures and is insertable through a guidewire lumen 32 formed in the catheter 12.

Figure 2A:
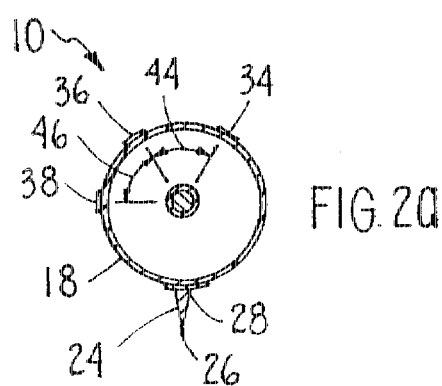
FIG. 2a is a cross-sectional view of the present invention along line 2a—2a in FIG. 1.

Finally, the present invention includes a series of radio-opaque markers each mounted to the outer surface of the balloon 18. More specifically, the present invention includes a distal marker 34, mounted near the distal end of the balloon 18, a proximal marker 36 mounted near the proximal end of the balloon 18, and an intermediate marker 38 mounted between the distal marker 34 and the proximal marker 36. Importantly, the markers 34, 36 and 38 are made of a material which is opaque to x-rays and are separated longitudinally, as just described, as well as radially. The longitudinal separation is apparent from examination of FIG. 1 where the longitudinal separation between distal marker 34 and intermediate marker 38 is shown and designated 40. Similarly, the longitudinal separation between proximal marker 36 and intermediate marker 38 is shown and designated 42. The radial separation between the markers 34, 36 and 38 is apparent from examination of FIG. 2 where the radial separation between distal marker 34 and proximal marker 36 is shown and designated 44. Similarly, the radial separation between proximal marker 36 and intermediate marker 38 is shown and designated 46.

OPERATION

Figure 2B:
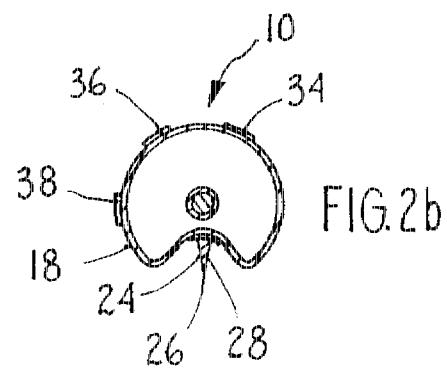
FIG. 2b is a view of FIG. 2a with a collapsed balloon.
Figure 3:
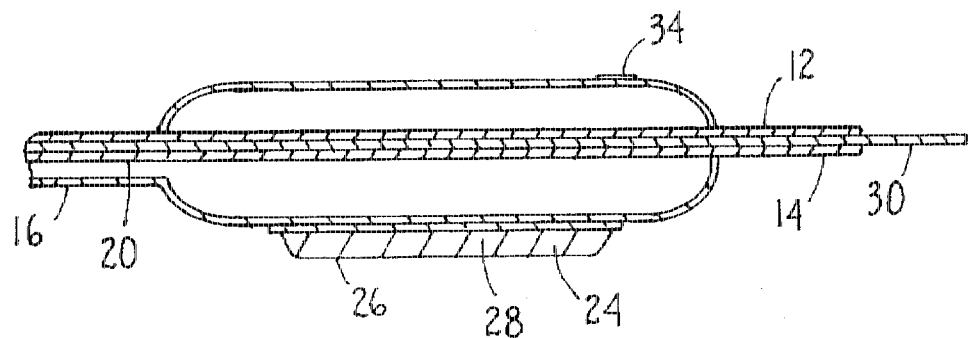
FIG. 3 is a cross-sectional view of the present invention along line 3—3 in FIG. 1.
Figure 4A:
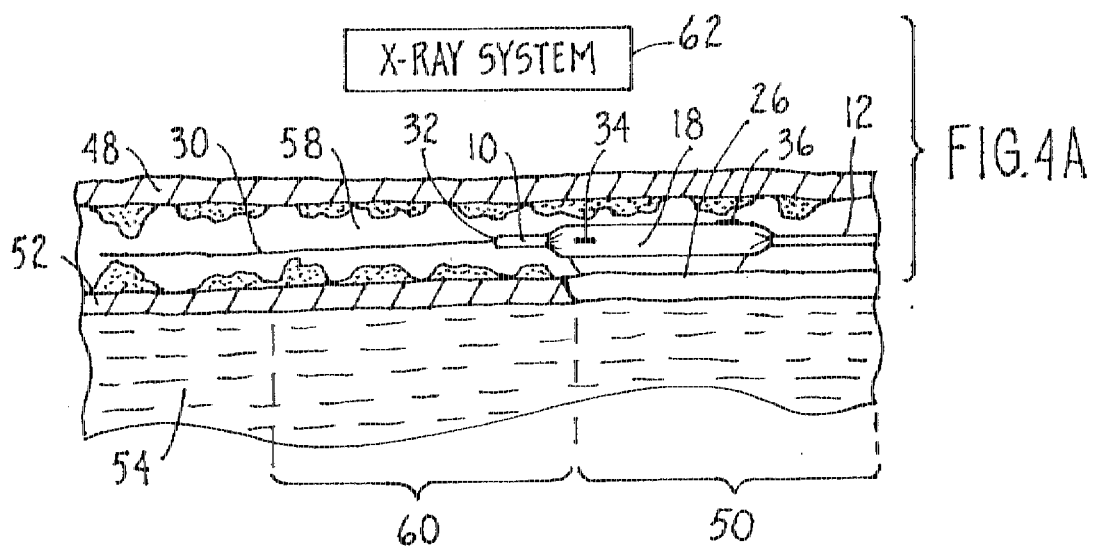
FIG. 4A is a longitudinal cross-sectional view of a coronary artery showing the present invention deployed to create an arterial transection.
Figure 5A:
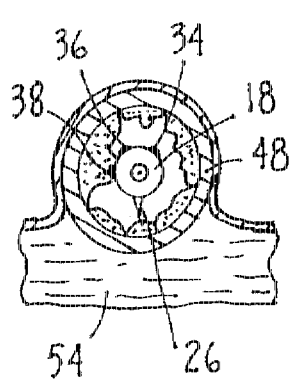
FIG. 5A is a lateral cross-sectional view of a coronary artery showing the present invention deployed to create an arterial transection.

Operational deployment of the present invention is best appreciated by initial reference to FIGS. 4A and 5A. More specifically, operation of the present invention begins with insertion of the distal end of the guidewire 30 into an artery, such as artery 48. The guidewire 30 is then advanced until the distal end of the guidewire 30 is positioned slightly past the region 50 where the initial transection is to be performed. Once the distal end of the guidewire 30 has been prepositioned, the guidewire's proximal, extracorporeal end, is inserted into the guidewire lumen 32. Insertion of the guidewire 30 into the guidewire lumen 32 allows the device 10 to be advanced over the guidewire 30 and into the artery 48. It will be appreciated that during advancement of balloon 18 through the artery 48, care must be taken to not unnecessarily incise the wall of artery 48 with the blade 24. This can be done in several ways. For one, as shown in FIG. 2b, the cutting edge of blade 24 can be protected by the collapsed balloon 18. In another way, a sheath catheter (not shown) can be used to position the balloon 18 near the stenosis. In either way the device 10 is positioned in the artery 48 so that the balloon 18 located near the region 50 where the initial transection is to be performed.

With the initial positioning of the balloon 18 complete, an X-ray imaging system 62 is activated to visualize the device 10 within the artery 48. In particular, the X-ray imaging system 62 provides a visual indication of the relative locations of the distal marker 34, proximal marker 36 and intermediate marker 38. Importantly, by examination of the these relative locations, the longitudinal and rotational position of the balloon 18 and, in particular the cutting edge 26, may be accurately determined. In this way, and as shown in FIG. 5A, the balloon 18 is oriented so that the cutting edge 26 is directed at the portion of the arterial wall 52 which is affixed to the cardiac tissue 54.

Figure 5B:
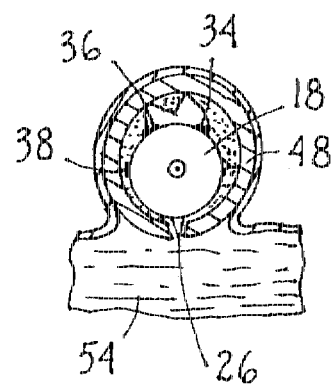
FIG. 5B is a lateral cross-sectional view of a coronary artery with the present invention shown in an expanded configuration to create an arterial transection.
Figure 5C:
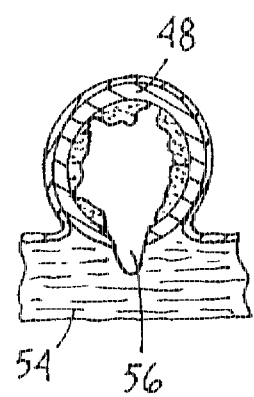
FIG. 5C is a lateral cross-sectional view of a coronary artery subsequent to creation of the arterial transection.

Once the cutting edge 26 has been accurately positioned using the X-ray imaging system 62, the fluid pump 22 may be activated to fill the balloon 18. Filling of the balloon 18, as best appreciated by reference to FIG. 5B, causes the cutting edge 26 to incise the arterial wall 52. Importantly, the incision 56 is positioned in the region of the arterial wall 52 which is adjacent to the cardiac tissue 54. In this way, the incision 56 and the balloon 18 enlarge the lumen 58 of the arterial vessel 48 without causing an uncontrolled loss of blood.

Figure 4B:
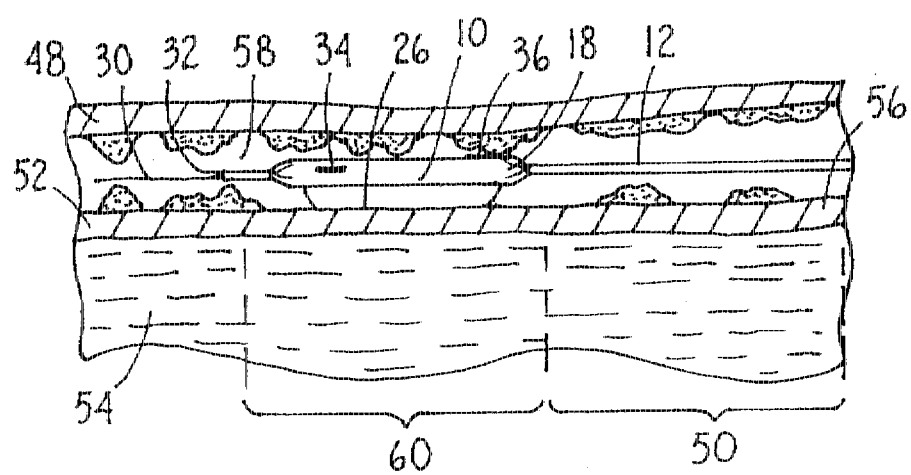
FIG. 4B is a longitudinal cross-sectional view of a coronary artery showing the present invention deployed to extend the arterial transection of FIG. 4A.

Creation of the incision 56 is followed by activation of the fluid pump 22 to withdraw fluid from the balloon 18 resulting, of course, in the deflation of the balloon 18. Deflation of the balloon 18 withdraws the cutting edge 26 of the blade 24 from the arterial wall 52. At this point, the device 10 may be withdrawn from the artery 48 completing the transection procedure and leaving the artery substantially as shown in Fib 5c with the incision 56 which eventually heals to enlarge the lumen of the artery. Alternatively, and as shown in FIG. 4B, the balloon 18 and cutting edge 26 may be repositioned to a region 60 where a subsequent transection is to be performed. Once the repositioning has been performed, the X-ray imaging system may be reactivated and the longitudinal and rotational position of the cutting edge 26 may be accurately selected by reference to the relative positions of the distal marker 34, proximal marker 36 and intermediate marker 38. The balloon 18 may then be reinflated to effect further transection of the arterial wall 52. In many cases, it will be desirable to use the previously described method to produce a single transection of selectable length.

While the particular device for transecting a coronary artery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for transecting a coronary artery which comprises:

a balloon;

a cutting element mounted on said balloon;

a radiopaque marker mounted on said balloon in a predetermined alignment with said cutting element, the radiopaque marker being positioned away from said cutting element;

means for orienting said balloon in accordance with said predetermined alignment with said cutting element in the coronary artery; and means for selectively inflating said balloon to transect the artery with said cutting element.

2. A device as recited in claim 1 wherein said cutting element is a blade.

3. A device as recited in claim 1 wherein said positioning means is a catheter.

4. A device as recited in claim 3 wherein said catheter is formed with an inflation lumen and a guidewire lumen.

5. A device as recited in claim 3 wherein said inflation lumen is in fluid communication with said balloon and with said means for inflating said balloon.

6. A device as recited in claim 1 wherein said radiopaque marker comprises a pair of spaced apart radiopaque markers and the means for orienting said balloon includes orienting the pair of radiopaque markers.

7. A method for transecting a coronary artery which comprises:

providing a device which comprises a selectively inflatable balloon having two radiopaque markers and a cutting element mounted thereon, the cutting element being in a predetermined alignment with the radiopaque markers;

positioning said balloon in the coronary artery;

visualizing said radiopaque markers; and rotating said balloon to place the two radiopaque markers in a predetermined interrelationship.

8. A method as recited in claim 7 further comprising the steps of:

inflating the balloon to transect the artery;

deflating the balloon after the inflating step;

repositioning the balloon in the coronary artery;

revisualizing said radiopaque markers;

rotating the balloon to place the radiopaque markers in a predetermined interrelationship; and reinflating the balloon to further transect the artery.

9. A method as recited in claim 8 wherein said further transection of said artery is a continuation of said transection of said artery.

10. A device for transecting a coronary artery which comprises:

expandable means, said expandable means movable between a first configuration wherein said expandable means has a reduced radius and a second configuration wherein said expandable means has an increased radius;

a cutting element mounted on said expandable means;

a pair of spaced apart radiopaque markers mounted on said expandable means in a predetermined alignment with said cutting element, said radiopaque markers being offset from said cutting element;

means for positioning said expandable means with said cutting element in the coronary artery;

means for orienting the cutting element by placing the pair of radiopaque markers in a predetermined interrelationship; and means for causing said expandable means to adopt said second configuration to transect the artery with said cutting element.

11. A device as recited in claim 10 wherein said expandable means is an inflatable balloon.

12. A device as recited in claim 11 wherein said positioning means is a catheter, said catheter formed with a inflation lumen connected in fluid communication with said balloon.

13. A device as recited in claim 12 further comprising a guidewire and wherein said catheter is formed with a guidewire lumen for receiving said guidewire.

14. A device as recited in claim 10 wherein said cutting element is a blade.

15. A device for transecting a coronary artery which comprises:

a generally cylindrical balloon having a longitudinal axis and a radius;

a cutting element mounted on said balloon;

a radiopaque marker mounted on said balloon in a predetermined alignment with said cutting element, said radiopaque marker including a distal stamp, a proximal stamp; and an intermediate stamp located between said distal stamp and said proximal stamp, with said intermediate stamp being radially offset from said distal stamp and said proximal stamp being radially offset from said distal stamp and from said intermediate stamp;

means for orienting said balloon in accordance with said predetermined alignment with said cutting element in the coronary artery; and means for selectively inflating said balloon to transect the artery with said cutting element.

16. A method for transecting a coronary artery which comprises:

providing a device which comprises a selectively inflatable balloon having a radiopaque marker and a cutting element mounted thereon, the cutting element being in a predetermined alignment with the radiopaque marker, said balloon is generally cylindrical and is defined by a longitudinal axis and a radius, said radiopaque marker comprises a distal stamp, a proximal stamp and an intermediate stamp located therebetween, with said intermediate stamp being radially offset from said distal stamp and said proximal stamp being radially offset from said distal stamp and from said intermediate stamp;

providing an X-ray imaging system;

positioning said balloon in the coronary artery;

activating said X-ray imaging system to visualize said radiopaque marker;

orienting the cutting element relative to said visualization of said radiopaque marker by rotating said balloon to place said distal stamp, said proximal stamp and said intermediate stamp in a predetermined interrelationship;

inflating the balloon to transect the artery with the cutting element;

deflating the balloon after the inflating step;

repositioning the balloon in the coronary artery;

reactivating said X-ray imaging system to visualize said radiopaque marker;

reorienting the cutting element relative to said visualization of said radiopaque marker; and reinflating the balloon to further transect the artery with the cutting element, said further transection of said artery being substantially a continuation of said transection of said artery.

17. A device for transecting a coronary artery which comprises:

expandable means, said expandable means movable between a first configuration wherein said expandable means has a reduced radius and a second configuration wherein said expandable means has an increased radius, wherein said expandable means is generally cylindrical having a longitudinal axis and a radius;

a cutting element mounted on said expandable means;

a radiopaque marker mounted on said expandable means in a predetermined alignment with said cutting element, said radiopaque marker comprises a distal stamp, a proximal stamp, and an intermediate stamp located between said distal stamp and said proximal stamp, with said intermediate stamp being radially offset from said distal stamp and said proximal stamp being radially offset from said distal stamp and from said intermediate stamp;

means for positioning said expandable means with said cutting element in the coronary artery; and means for causing said expandable means to adopt said second configuration to transect the artery with said cutting element.

* * * * *